United States Patent
Murray et al.

(10) Patent No.: US 6,653,514 B1
(45) Date of Patent: Nov. 25, 2003

(54) REMOVAL OF PHOSPHORUS-CONTAINING IMPURITIES FROM AN OLEFIN FEEDSTOCK

(75) Inventors: Brendan Dermot Murray, Houston, TX (US); David Michael Singleton, Houston, TX (US); Zaida Diaz, Houston, TX (US)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 09/566,461

(22) Filed: May 8, 2000

(51) Int. Cl.⁷ .................. C07C 27/20; C07C 27/22; C07C 27/24; C07C 29/15
(52) U.S. Cl. ............... 568/909; 585/329; 585/512; 585/523; 585/527; 585/823
(58) Field of Search .............. 568/909; 585/329, 585/512, 823, 527, 523

(56) References Cited

U.S. PATENT DOCUMENTS

| | | |
|---|---|---|
| 3,674,886 A | 7/1972 | Komatsu et al. |
| 3,676,523 A | 7/1972 | Mason |
| 3,686,351 A | 8/1972 | Mason |
| 3,737,475 A | 6/1973 | Mason |
| 3,770,619 A | 11/1973 | Derrien et al. |
| 4,020,121 A | 4/1977 | Kister et al. |
| 4,076,842 A | 2/1978 | Plank et al. |
| 4,351,980 A | 9/1982 | Reusser et al. |
| 4,551,443 A | 11/1985 | Hudson |
| 4,717,785 A * | 1/1988 | Paxson ................ 585/823 |
| 5,072,057 A | 12/1991 | Oswald et al. |
| 5,112,519 A | 5/1992 | Giacobbe et al. |
| 5,376,393 A | 12/1994 | Nardelli |
| 5,378,439 A | 1/1995 | Delobel et al. ........ 423/210 |
| 5,510,306 A | 4/1996 | Murray ................. 502/64 |
| 5,618,467 A | 4/1997 | Turk et al. |
| 5,780,694 A | 7/1998 | Singleton |
| 5,849,960 A * | 12/1998 | Singleton et al. ........ 568/909 |
| 6,084,140 A | 7/2000 | Kitamura et al. |
| 6,492,568 B1 | 12/2002 | Murray et al. |

OTHER PUBLICATIONS

"Sasol Detergent Alcohols", Preliminary Sasol R&D Technical Bulletin; Oct. 1995.
U.S. patent application Ser. No. 09/566,460, Murray et al., filed May 8, 2000.
U.S. patent application Ser. No. 10/216,522, Murray et al., filed Aug. 9, 2000.
U.S. patent application Ser. No. 10/318,718, Himelfarb et al., filed Dec. 13, 2002.
Molecular Sieves Principles of Synthesis and Identification, R. Szostak, Van Nostrand Reinhold, 1989, pp. 26–27 and 83.
"Verfahren Zur Katalytischen Oligomerisierung Von Monoolefinen" Research Disclosure, Kenneth Mason Publications, Hampshire, GB, No. 415, Nov. 1998, pp. 1445–1451, XP000824939.

* cited by examiner

Primary Examiner—Johann Richter
Assistant Examiner—Elvis O. Price

(57) ABSTRACT

The invention pertains to a process of removing phosphorous-containing impurities and preferably also dienes, from an olefin stream using a sorbent selected from the group consisting of an acidic ion exchange resin, an acidic zeolite, an acidic alumina, a neutral alumina, and an activated carbon. The olefin stream preferably comprises primarily olefins having at least 6 carbon atoms.

160 Claims, No Drawings

REMOVAL OF PHOSPHORUS-CONTAINING IMPURITIES FROM AN OLEFIN FEEDSTOCK

CROSS-REFERENCE TO RELATED APPLICATIONS

The present application is related to U.S. Pat. No. 6,388,162 B1 and the following pending applications: U.S. patent application Ser. No. 10/216,522, filed Aug. 9, 2002; U.S. patent application Ser. No. 09/566,460, and U.S. patent application Ser. No. 09/566,463, which were filed May 8, 2000.

FIELD OF THE INVENTION

The invention pertains to a process of removing contaminants from olefin feedstocks using sorbents. In a preferred embodiment, phosphorus-containing impurities, most preferably organophosphines and/or organophosphine oxides, are removed from the olefin feedstock using an acidic or a neutral sorbent. The sorbent preferably is selected from the group consisting of an acidic ion exchange resin, an acidic zeolite, an acidic alumina, a neutral alumina, and an activated carbon. Preferred olefin feedstocks are those made by oligomerizing ethylene to linear olefins having from about 6 to about 36 carbon atoms, preferably from about 11 to about 20 carbon atoms, and most preferably from about 14 to about 18 carbon atoms.

BACKGROUND OF THE INVENTION

Depending upon the method of their production, olefin feedstocks may comprise a variety of impurities. Impurities found in olefins that are produced by oligomerization of ethylene units include phosphorous-containing impurities, including but not necessarily limited to organophosphines and organophosphine oxides. These phosphorous-containing impurities are largely removed from many olefin streams during the process of distillation to separate various "cuts" of olefins. Unfortunately, the organophosphines and organophosphine oxides found in $C_{14}$–$C_{18}$ streams tend to codistill with the $C_{14}$–$C_{18}$ in the product, making it difficult, if not impossible to remove these phosphine impurities by simple distillation.

$C_6$–$C_{36}$ olefins have utility in the fields of paper and pulp processing, drilling fluids, and machine or metal working oils. Alcohols of such olefins have commercial importance in a variety of applications, including detergents, soaps, surfactants, and freeze point depressants in lubricating oils. These alcohols are produced by a number of commercial processes, such as by oxo or hydroformylation of long chain olefins. In many of these applications, the olefin feedstocks are treated using acid catalysts.

Unfortunately, any phosphorus-containing impurities in these olefin feedstocks will negatively affect acid catalysts. The phosphorous-containing moieties are basic in nature and will neutralize the active acid sites of the catalyst, which lowers catalyst activity and performance. The organophosphine moeities may even cause the olefins to oligomerize into undesirable forms.

Methods are needed to reduce the phosphorous-content of olefin feedstocks.

SUMMARY OF THE INVENTION

The present invention provides a process for purifying an olefin feed comprising a content of phosphorus-containing impurities. The process comprises contacting the olefin feed with a sorbent selected from the group consisting of an acidic ion exchange resin, an acidic zeolite, an acidic alumina, a neutral alumina, and an activated carbon under conditions and for a time effective to reduce the content of phosphorus-containing impurities and to produce a purified olefin feed.

DETAILED DESCRIPTION OF THE INVENTION

The present invention provides a process and sorbents which efficiently and effectively reduce the content of phosphorous-containing impurities in olefin streams. In a preferred embodiment, the content is reduced to about 1 ppm or less, preferably about 0.5 ppm or less, most preferably to about 0.1 ppm or less. Given sufficient run time, the sorbents reduce the content of phosphorous-containing impurities in the olefin stream to parts per billion (ppb) levels. In a preferred embodiment the sorbents of the present invention may be used to remove dienes from the olefin stream.

The invention may be used to treat substantially any olefin stream. Preferred olefin streams are linear olefin streams made by oligomerizing ethylene. Some of the known processes for oligomerizing ethylene use organophosphorus compounds that result in phosphorus as a contaminant in the resulting olefin stream. A preferred commercially available olefin feed for the treatment of the present invention is the product marketed in the United States by Shell Chemical Company under the trademark NEODENE®. In a preferred embodiment, the olefin feedstock is treated before exposure to an acid catalyst, or before exposure to other conditions which would be adversely affected by the basic nature of phosphorus-containing contaminants.

In a most preferred embodiment, the olefin stream is the feedstock for the skeletal isomerization catalyst used in the method described in U.S. Pat. No. 5,849,960, which has been incorporated herein by reference. The olefins used in the feed to this skeletal isomerization catalyst are mono-olefins having at least 6 carbon atoms, preferably having from about 11 to about 20 carbon atoms, and most preferably having from about 14 to about 18 carbon atoms.

In general, the olefins in the feed to the skeletal isomerization catalyst are predominately linear. While the olefin feed can contain some branched olefins, the olefin feed processed for skeletal isomerization preferably contains greater than about 50 percent, more preferably greater than about 70 percent, and most preferably greater than about 80 mole percent or more of linear olefin molecules.

The olefin feed to the skeletal isomerization catalyst does not consist of 100% olefins, and usually contains a distribution of mono-olefins having different carbon lengths, with at least 50 wt. % of the olefins being within the stated carbon chain range or digit, however specified. Preferably, the olefin feed will contain greater than 70 wt. %, more preferably about 80 wt. % or more of mono-olefins in a specified carbon number range, the remainder of the product being olefins of other carbon number or carbon structure, diolefins, paraffins, aromatics, and other impurities resulting from the synthesis process. The location of the double bond is not limited. The olefin feed composition may comprise alpha olefins, internal olefins, or a mixture thereof.

The sorbent of the present invention may be substantially any suitable sorbent capable of sorbing phosphorus-containing impurities, preferably neutral and acidic sorbents, most preferably acidic sorbents. Suitable neutral sorbents include neutral aluminas, activated carbons, and metal impregnated activated carbons, such as BARNEBEY CE, a silver impregnated carbon available from Barnebey & Sutcliffe. Suitable acidic sorbents include, but are not necessarily limited to acidic ion exchange resins and acidic aluminas. Suitable commercially available aluminas include, but are not necessarily limited to acidic and neutral activated aluminas, such as those available from Aldrich Chemical Co. and Selecto Scientific Co. Also suitable are the modified aluminas, such as SELEXSORB CDO 200, SELEXSORB CDX, AND SELEXSORB CD. These aluminas are modified to improve the sorption of polar organics, and are commercially available from Alcoa Industrial Chemicals. Also suitable are acidic ion exchange resins, such as AMBERLYST 15 RESIN, available from Rohm & Haas Chemical Co.

The surface area of the sorbent is not critical, but preferably is at least about 10 $m^2/g$ in order to provide sufficient contact between the sorbent and the olefin stream. In a preferred embodiment, the sorbent has a surface area of from about 100 $m^2/g$ to about 900 $m^2/g$. It is preferred for the sorbent particles to be as small as possible; however, if the size of the particles is too small, the pressure drop through the bed becomes too large. Very small particles also are difficult to retain in the sorbent bed. The particles may have substantially any form, including but not necessarily limited to spherical form, tablet form, cylindrical form, multilobed cylindrical forms, and their corresponding hollow counterparts. In a preferred embodiment, the particles have a diameter of from about 50 mesh to about 6 mm, preferably about 0.8 mm (1/32 inch) to about 1.6 mm (1/16 inch), most preferably about 0.8 mm. The length of the particles is not critical, with suitable lengths including, but not necessarily limited to less than about 10 mm, preferably from about 3 mm to about 5 mm.

In a preferred embodiment, the sorbent is an acidic ion exchange resin, most preferably AMBERLYST 15, which generally may be used as received from the supplier.

In another preferred embodiment, the sorbent is an alumina extrudate which is extruded as a paste using an acidic or neutral alumina powder. The "paste" is extruded or otherwise molded into a multilobed cylindrical form. The resulting material preferably is dried at temperatures of at least about 100° C. and calcined at about 500° C. or more in the presence of flowing air in a muffle furnace or purged high temperature air drier or rotary calciner.

Preferably, the olefin feedstock is contacted in the liquid phase in a reaction zone with the sorbent of the present invention at effective process conditions to reduce the content of phosphorous-containing impurities in the feedstock, i.e., an effective temperature, pressure, and LHSV (Liquid Hourly Space Velocity). A preferred embodiment of a reactor system for the process is an upflow or downflow fixed bed reactor. An upflow reactor is preferred for better wetting of the sorbent bed. The temperature employed may vary. Although not limited to a particular temperature, best results will be obtained if the process is conducted at temperatures of from about 0° C. to about 100° C., preferably from about 10° C. to about 50° C. The pressures may vary over a range including but not limited to autogeneous pressures and pressures in the range of from about 0.01 MPa to about 50 MPa. A preferred pressure is in the range of from about 0.1 MPa to about 10 MPa. Pressures outside of the stated ranges may be used and are not excluded from the scope of the invention.

The feedstock may flow at a wide range of liquid hourly space velocities (LHSV), defined as liquid feed per hour per volume of sorbent. The LHSV is calculated as follows:

$$\text{feed} \times \frac{\text{Volume of olefin containing l}}{\text{Volume of sorbent hr}}$$

The lower the LHSV, the greater will be the reduction in content of phosphorus-containing impurities in the feedstock. The LHSV generally is from about 0.01 hr to about 10 $hr^{-1}$, preferably from about 0.1 $hr^{-1}$ to about 1 $hr^{-1}$.

The process is continued for a period of time sufficient to achieve a desired reduction in the content of phosphorus-containing impurities in the olefin stream. The content of phosphorus-containing impurities preferably is reduced to about 1 ppm or less, most preferably to about 0.1 ppm or less. The reaction cycle time may vary from tenths of seconds to a number of hours. The reaction cycle time is largely determined by the reaction temperature, the pressure, the sorbent selected, the liquid hourly space velocity, and the desired reduction in content of phosphorus containing impurities.

At some point, the sorbent becomes saturated, and must be regenerated. The sorbent may be regenerated by exposing the sorbent to an oxygen-containing atmosphere at a temperature of from about 200° C. to about 550° C., preferably from about 450° C. to about 600° C. Suitable oxygen containing atmospheres include, but are not necessarily limited to air, oxygen gas, and a combination of oxygen gas with nitrogen gas. A preferred gas is a commercially available combination comprising about 1% oxygen, with the remainder being nitrogen. After exposure to these increased temperatures for a period of time of from about 0.5 hour to about 100 hours, the bed is cooled to at least about 100° C., and preferably to about 25° C., or ambient temperature, in order to avoid overheating upon reuse. The cooled bed is purged with nitrogen or air before reuse in the process. Ten regeneration cycles under these conditions have been shown to produce no loss in sorbent capacity. Some slight loss in sorbent capacity was seen beginning after 10 regeneration cycles.

Typical olefin feedstocks comprise from about 100 ppm to about 2000 ppm dienes that tend to lower the efficiency of skeletal isomerization catalysts. The sorbents of the present invention are useful for sorbing dienes from the feedstream, both before and after the olefin feedstock contacts the skeletal isomerization catalyst. In a preferred embodiment, the sorbent of the present invention may be used to sorb dienes from initial olefin streams before contact with the isomerization catalyst in addition to lowering the phosphorus content of the olefin stream. Substantially all of the sorbents listed herein may be used for this purpose. A preferred sorbent for removing dienes is alumina.

$C_6$ to $C_{36}$ olefins have a variety of uses, including but not necessarily limited to uses in paper processing, drilling fluids, and machine or metal working. In a preferred embodiment, the olefin feedstock is converted to branched primary alcohols in the process described in U.S. Pat. No. 5,849,960, incorporated herein by reference. Most preferably, the olefin feedstock is treated before the olefins are fed to a skeletal isomerization catalyst, as described in U.S. Pat. No. 5,849,960. A preferred skeletal isomerization catalyst for use in conjunction with the present invention is a hydrogen ferrierite catalyst, as described in U.S. Pat. No. 5,510,306, incorporated herein by reference.

In a preferred embodiment, the skeletally isomerized olefins are converted to any of a broad range of surfactants, including nonionic, anionic, cationic, and amphoteric surfactants, with a degree of branching of at least 1.0. The skeletally isomerized olefins serve as a surfactant intermediate. Specifically, the skeletally isomerized olefins serve as the hydrophobic moiety of the surfactant molecule, while the moiety added to the olefin during the conversion process serves as the hydrophile.

The invention will be better understood with reference to the following examples, which are illustrative only and not intended to limit the invention to any particular embodiment.

EXAMPLE I

NEODENE®16 containing 22 ppm phosphorus was placed in a jar with the sorbents in the following table and shaken intermittently by a flat bed shaker over a period of 15 hours at 23 C. to achieve equilibration. The NEODENE® to sorbent weight ratio was 100. After equilibration, the NEODENE® was separated from the sorbent and analyzed for phosphorus using inductively coupled plasma (ICPO). P loadings on the sorbents were calculated from the change in the P content of NEODENE® due to equilibration with the sorbents. The results are given in the following Table:

| Sorbent | Equilibrium P (ppm) | P loading (g/100 g sorbent) |
|---|---|---|
| SELEXSORB CDO 200 | 5.1 | 0.17 |
| SELEXSORB CDX | 2.9 | 0.19 |
| SELEXSORB CD | 4.2 | 0.18 |
| ALUMINA 24033-13 AL* | 6 | 0.16 |
| ALUMINA 24033-13 NEUTRAL** | 4 | 0.18 |
| ALUMINA ABA-6000 ACIDIC*** | 3.8 | 0.18 |
| ALUMINA ABA-6000 BASIC*** | 6 | 0.16 |
| ALUMINA ABA-6000 NEUTRAL*** | 5.5 | 0.17 |

*150 mesh acidic alumina from Aldrich Chemical Co.
**Neutral alumina from Aldrich.
***Aluminas obtained from Selecto Scientific.

All of the sorbents were effective to remove phosphorus from the feed, with the more acidic sorbents being slightly more effective.

EXAMPLE II

The procedures of Example I were repeated using different sorbents using a feed containing 18 ppm P with the following results:

| Sorbent | Equilibrium P (ppm) | P loading (g/100 g sorbent) |
|---|---|---|
| BARNABEY SE carbon | 7 | 0.11 |

The sorbent was effective to remove phosphorus from the feed.

EXAMPLE III

The procedures of Example I were repeated using the following sorbent and a feed containing 16.8 ppm P with the following results:

| Sorbent | Equilibrium P (ppm) | P loading (g/100 g sorbent) |
|---|---|---|
| SELECTO SCIENTIFIC NEUTRAL ALUMINA | 2.9 | 0.14 |

The sorbent was effective to remove phosphorus from the feed.

EXAMPLE IV

The procedures of Example I were repeated using the following sorbents and a feed containing 16.4 ppm P with the following results:

| Sorbent | Equilibrium P (ppm) | P loading (g/100 g sorbent) |
|---|---|---|
| AMBERLYST 15 resin | <2 | >0.14 |
| MOLECULAR SIEVES 5A | 14.6 | 0.02 |
| ZSM-5 (Si/Al = 40) | 12.5 | 0.04 |
| ZEOLON 200H | 10.6 | 0.06 |

The results demonstrate that the foregoing sorbents are effective to remove phosphorus from the feed.

EXAMPLE V

The procedures of Example I were repeated using the following sorbents, a feed containing 24 ppm P, and varying the NEODENE® to sorbent weight ratio, as indicated, with the following results:

| Sorbent | NEODENE ® to sorbent weight ratio | Equilibrium P (ppm) | P loading (g/100 g sorbent) |
|---|---|---|---|
| ZEOLITE USY-H form | 100 | 10.9 | 0.13 |
| ZEOLITE USY-H form | 200 | 16.1 | 0.16 |
| ZEOLITE USY-H form | 300 | 18.4 | 0.17 |
| ZEOLITE USY-H form | 500 | 21 | 0.15 |
| AMBERLYST 15 resin | 100 | <0.6 | 0.23 |
| AMBERLYST 15 resin | 200 | 1.6 | 0.45 |
| AMBERLYST 15 resin | 300 | 8 | 0.48 |
| AMBERLYST 15 resin | 500 | 11.9 | 0.61 |

The foregoing results again demonstrate that AMBERLYST 15 is effective in removing phosphorus from the feedstream.

EXAMPLE VI

A series of tests were performed to illustrate the nature of the invention and its impact on skeletal isomerization of detergent range olefins.

A. Preparation of Treated Feed

A glass column with an inner diameter of 50 mm was packed with 150 mesh neutral, activated aluminum oxide (Brockmann I) obtained from Aldrich Chemical Company to produce a bed 400 mm in length. 20 liters of a mixture of primarily linear $C_{14-19}$ olefins, obtained from and commercially available from Shell Chemical Company, was passed through the packed bed at a weight hourly space velocity of 0.5 per hour and the liquid effluent was collected in a container purged with nitrogen. The diene content of the mixed $C_{14}$–$C_{19}$ olefins was reduced from 270 ppm to 20 ppm in the process.

B. Preparation of Skeletal Isomerization Catalyst

A catalyst was prepared in accordance with example C of U.S. Pat. No. 5,510,306, reproduced in part herein for convenience. An ammonium-ferrierite having a molar silica to alumina ratio of 62:1, a surface area of 369 square meters per gram (P/Po=0.03), a soda content of 480 ppm and n-hexane sorption capacity of 7.3 g per 100 g of zeolite was used as the starting zeolite. The catalyst components were mulled using a Lancaster mix muller. The mulled catalyst material was extruded using a 2.25 inch Bonnot pin barrel extruder.

The catalyst was prepared using 1 weight percent acetic acid and 1 weight percent citric acid. The Lancaster mix muller was loaded with 645 grams of ammonium-ferrierite (5.4% LOI) and 91 grams of CATAPAL D ® alumina , purchased from Vista Chemical of Houston, Texas, (LOI of 25.7%). The alumina was blended with the ferrierite for 5 minutes during which time 152 milliliters of de-ionized water was added. A mixture of 6.8 grams glacial acetic acid, 7.0 grams of citric acid and 152 milliliters of de-ionized water was added slowly to the muller in order to peptize the alumina. The mixture was mulled for 10 minutes. 0.20 Grams of tetraammine palladium nitrate in 153 grams of de-ionized water were then added slowly as the mixture was mulled for a period of 5 additional minutes. Ten grams of METHOCEL F4M®, purchased from Dow Chemical Company of Midland, Michigan, hydroxypropyl methylcellulose was added and the zeolite/alumina mixture was mulled for 15 additional minutes. The extrusion mix had an LOI of 43.5%. The 90:10 zeolite/alumina mixture was transferred to the 2.25 inch Bonnot extruder and extruded using a die plate with $\frac{1}{16}$" holes.

The moist extrudates were tray dried in an oven heated to 150° C. for 2 hours, and the temperature was then increased to 175° C. for 4 hours. After drying, the extrudates were broken manually. The extrudates were calcined in flowing air at 500° C. for two hours.

C. Skeletal Isomerization Using Treated Feed from A

Skeletal isomerization of the mixture of alumina treated $C_{14}$–$C_{19}$ olefins obtained was conducted using an olefin isomerization reactor. A stainless steel tube, 25.4 mm OD, 15 mm ID and 685 mm long was used to contain the catalyst. One end of the tube was screwed into a stainless steel head equipped with a thermowell which extended up the center of the tube. The tube was loaded with a small plug of glass wool, then filled to a depth of 150 mm with 20 mesh silicon carbide, and then a small plug of glass wool was added above the SiC. 6.00 grams of the catalyst described above was admixed with 45 grams of 60–80 mesh SiC and added in three parts to distribute it evenly inside the reactor tube. Another piece of glass wool was added and the remaining volume of the reactor tube was filled with 20 mesh SiC topped by a final piece of glass wool. The tube was screwed into another stainless steel head and a multipoint thermocouple was inserted into the thermowell to allow the temperature above, below, and inside the catalyst bed to be monitored. The reactor tube then was installed inside of an electric furnace. Connections were made at the top of the reactor to allow nitrogen and the olefin to be passed through the reactor. The bottom of the reactor was connected to a condenser and a product collection system.

Nitrogen at a rate of 6 liters per hour was passed through the reactor while the catalyst bed was heated to 290° C. over a period of 2 hours. A mixture of $C_{14}$–$C_{19}$ olefins, prepared as in Section A (with diene content of 20 ppm), was pumped to the reactor at a rate of 60.0 grams per hour, allowed to mix with the incoming nitrogen and then passed through the catalyst bed. During the testing the inlet pressure was held at 1.6 psig while the outlet pressure of the reactor was maintained at 1.0 psig. The liquid product was collected in a 5 gallon vessel while the uncondensed gas was passed through a gas meter. Sampling ports incorporated in the reactor allowed the liquid and gas products to be analyzed regularly. The products were analyzed by gas chromatography. The results of the testing are presented in the Table below.

| Feedstock | Untreated Mixture of Linear $C_{14}$–$C_{19}$ Olefins | Alumina Treated $C_{14}$–$C_{19}$ Olefins | Selectively Hydrogenated $C_{14}$–$C_{19}$ Olefins |
|---|---|---|---|
| Diene Content | 270 | 20 | 160 |
| Time on Stream, Hr. | | % Branching In Liquid Product | |
| 18 | 82 | 94 | 93 |
| 42 | 77 | 93 | 92 |
| 70 | 64 | 92 | 90 |
| 91 | 54 | 91 | 88 |
| 114 | 48 | 90 | 85 |
| 135 | 43 | 88 | 82 |

The level of branching in the isomerized product was significantly higher when the dienes were first sorbed by passage of the $C_{14}$–$C_{19}$ olefins through an alumina bed.

Persons of ordinary skill in the art will recognize that many modifications may be made to the present invention without departing from the spirit and scope of the present invention. The embodiment described herein is meant to be illustrative only and should not be taken as limiting the invention, which is defined in the following claims.

We claim:

1. A process of making a branched primary alcohol composition, comprising:

providing an olefin feed comprising a content of phosphorus-containing impurities;

providing one or more sorbents selected from the group consisting of an acidic zeolite, an acidic alumina, a neutral alumina, and an activated carbon, said one or more sorbents being adapted to sorb a sufficient amount of phosphorous containing impurities to produce a purified olefin feed, said sorbent comprising particles having a diameter of from about 0.8 mm ($\frac{1}{32}$ inch) to about 1.6 mm ($\frac{1}{16}$ inch); and contacting said olefin feed with said one or more sorbents under conditions and for a time effective to produce said purified olefin feed;

contacting said purified olefin feed with a skeletal isomerization catalyst under conditions effective to yield skeletally isomerized olefins; and converting said skeletally isomerized olefins into said primary alcohol composition.

2. The process of claim 1 wherein said sorbent comprises particles having a diameter of about 0.8 mm.

3. The process of claim 1 wherein said sorbent comprises alumina.

4. The process of claim 2 wherein said sorbent comprises alumina.

5. The process of claim 1 wherein said sorbent has a surface area of from about 100 m$^2$/g to about 900 m$^2$/g.

6. The process of claim 2 wherein said sorbent has a surface area of from about 100 m$^2$/g to about 900 m$^2$/g.

7. The process of claim 3 wherein said sorbent has a surface area of from about 100 m²/g to about 900 m²/g.

8. The process of claim 4 wherein said sorbent has a surface area of from about 100 m²/g to about 900 m²/g.

9. The process of claim 1 wherein said LHSV is from about 0.01 hr⁻¹ to about 10 hr⁻¹.

10. The process of claim 1 Wherein said LHSV is from about 0.1 hr⁻¹ to about 1 hr⁻¹.

11. The process of claim 2 wherein said LHSV is from about 0.01 hr⁻¹ to about 10 hr⁻¹.

12. The process of claim 2 wherein said LHSV is from about 0.1 hr⁻¹ to about 1 hr⁻¹.

13. The process of claim 3 wherein said LHSV is from about 0.01 hr⁻¹ to about 10 hr⁻¹.

14. The process of claim 3 wherein said LHSV is from about 0.1 hr⁻¹ to about 1 hr⁻¹.

15. The process of claim 4 wherein said LHSV is from about 0.01 hr⁻¹ to about 10 hr⁻¹.

16. The process of claim 4 wherein said LHSV is from about 0.1 hr⁻¹ to about 1 hr⁻¹.

17. The process of claim 5 wherein said LHSV is from about 0.01 hr⁻¹ to about 10 hr⁻¹.

18. The process of claim 5 wherein said LHSV is from about 0.1 hr⁻¹ to about 1 hr⁻¹.

19. The process of claim 6 wherein said LHSV is from about 0.01 hr⁻¹ to about 10 hr⁻¹.

20. The process of claim 6 wherein said LHSV is from about 0.1 hr⁻¹ to about 1 hr⁻¹.

21. The process of claim 7 wherein said LHSV is from about 0.01 hr⁻¹ to about 10 hr⁻¹.

22. The process of claim 7 wherein said LHSV is from about 0.1 hr⁻¹ to about 1 hr⁻¹.

23. The process of claim 8 wherein said LHSV is from about 0.01 hr⁻¹ to about 10 hr⁻¹.

24. The process of claim 8 wherein said LHSV is from about 0.1 hr⁻¹ to about 1 hr⁻¹.

25. The process of claim 1 further comprising regenerating said sorbent.

26. The process of claim 2 further comprising regenerating said sorbent.

27. The process of claim 3 further comprising regenerating said sorbent.

28. The process of claim 4 further comprising regenerating said sorbent.

29. The process of claim 25 wherein said regenerating comprises exposing said sorbent to regeneration conditions comprising a quantity of oxygen and a temperature effective to regenerate said sorbent.

30. The process of claim 26 wherein said regenerating comprises exposing said sorbent to regeneration conditions comprising a quantity of oxygen and a temperature effective to regenerate said sorbent.

31. The process of claim 27 wherein said regenerating comprises exposing said sorbent to regeneration conditions comprising a quantity of oxygen and a temperature effective to regenerate said sorbent.

32. The process of claim 28 wherein said regenerating comprises exposing said sorbent to regeneration conditions comprising a quantity of oxygen and a temperature effective to regenerate said sorbent.

33. The process of claim 1 wherein said converting comprises hydroformylating said skeletally isomerized olefin.

34. The process of claim 2 wherein said converting comprises hydroformylating said skeletally isomerized olefin.

35. The process of claim 3 wherein said converting comprises hydroformylating said skeletally isomerized olefin.

36. The process of claim 4 wherein said converting comprises hydroformylating said skeletally isomerized olefin.

37. The process of claim 1 wherein said purified olefin feed consists of about 1 ppm or less of said phosphorous-containing impurities.

38. The process of claim 2 wherein said purified olefin feed consists of about 1 ppm or less of said phosphorous-containing impurities.

39. The process of claim 3 wherein said purified olefin feed consists of about 1 ppm or less of said phosphorous-containing impurities.

40. The process of claim 4 wherein said purified olefin feed consists of about 1 ppm or less of said phosphorous-containing impurities.

41. The process of claim 1 wherein said purified olefin feed consists of about 0.5 ppm or less of said phosphorous-containing impurities.

42. The process of claim 2 wherein said purified olefin feed consists of about 0.5 ppm or less of said phosphorous-containing impurities.

43. The process of claim 3 wherein said purified olefin feed consists of about 0.5 ppm or less of said phosphorous-containing impurities.

44. The process of claim 4 wherein said purified olefin feed consists of about 0.5 ppm or less of said phosphorous-containing impurities.

45. A process of making a branched primary alcohol composition, comprising:

providing an olefin feed comprising a content of phosphorus-containing impurities and a quantity of dienes;

providing one or more sorbents selected from the group consisting of an acidic zeolite, an acidic alumina, a neutral alumina, and an activated carbon, said one or more sorbents being adapted to sorb a sufficient amount of said phosphorous containing impurities and a sufficient concentration of said dienes to produce a purified olefin feed; and contacting said olefin feed with said one or more sorbents under conditions and for a time effective to produce said purified olefin feed;

contacting said purified olefin feed with a skeletal isomerization catalyst under conditions effective to yield skeletally isomerized olefins; and converting said skeletally isomerized olefins into said primary alcohol composition.

46. The process of claim 45 wherein said sorbent comprises particles having a diameter of from about 0.8 mm (1/32 inch) to about 1.6 mm (1/16 inch).

47. The process of claim 45 wherein said sorbent comprises particles having a diameter of about 0.8 mm.

48. The process of claim 45 wherein said sorbent comprises alumina.

49. The process of claim 46 wherein said sorbent comprises alumina.

50. The process of claim 47 wherein said sorbent comprises alumina.

51. The process of claim 45 wherein said sorbent has a surface area of from about 100 m²/g to about 900 m²/g.

52. The process of claim 46 wherein said sorbent has a surface area of from about 100 m²/g to about 900 m²/g.

53. The process of claim 47 wherein said sorbent has a surface area of from about 100 m²/g to about 900 m²/g.

54. The process of claim 48 wherein said sorbent has a surface area of from about 100 m²/g to about 900 m²/g.

55. The process of claim 49 wherein said sorbent has a surface area of from about 100 m²/g to about 900 m²/g.

56. The process of claim 50 wherein said sorbent has a surface area of from about 100 m²/g to about 900 m²/g.

57. The process of claim 45 wherein said LHSV is from about 0.01 hr⁻¹ to about 10 hr⁻¹.

58. The process of claim 45 wherein said LHSV is from about 0.1 hr⁻¹ to about 1 hr⁻¹.

59. The process of claim 46 wherein said LHSV is from about 0.01 hr⁻¹ to about 10 hr⁻¹.

60. The process of claim 46 wherein said LHSV is from about 0.1 hr⁻¹ to about 1 hr⁻¹.

61. The process of claim 47 wherein said LHSV is from about 0.01 hr⁻¹ to about 10 hr⁻¹.

62. The process of claim 47 wherein said LHSV is from about 0.1 hr⁻¹ to about 1 hr⁻¹.

63. The process of claim 48 wherein said LHSV is from about 0.01 hr⁻¹ to about 10 hr⁻¹.

64. The process of claim 48 wherein said LHSV is from about 0.01 hr⁻¹ to about 1 hr⁻¹.

65. The process of claim 49 wherein said LHSV is from about 0.01 hr⁻¹ to about 1 hr⁻¹.

66. The process of claim 49 wherein said LHSV is from about 0.01 hr⁻¹ to about 1 hr⁻¹.

67. The process of claim 50 wherein said LHSV is from about 0.01 hr⁻¹ to about 10 hr⁻¹.

68. The process of claim 50 wherein said LHSV is from about 0.1 hr⁻¹ to about 1 hr⁻¹.

69. The process of claim 51 wherein said LHSV is from about 0.01 hr⁻¹ to about 10 hr⁻¹.

70. The process of claim 51 wherein said LHSV is from about 0.1 hr⁻¹ to about 1 hr⁻¹.

71. The process of claim 52 wherein said LHSV is from about 0.01 hr⁻¹ to about 10 hr⁻¹.

72. The process of claim 52 wherein said LHSV is from about 0.1 hr⁻¹ to about 1 hr⁻¹.

73. The process of claim 45 further comprising regenerating said sorbent.

74. The process of claim 46 further comprising regenerating said sorbent.

75. The process of claim 47 further comprising regenerating said sorbent.

76. The process of claim 48 further comprising regenerating said sorbent.

77. The process of claim 49 further comprising regenerating said sorbent.

78. The process of claim 50 further comprising regenerating said sorbent.

79. The process of claim 73 wherein said regenerating comprises exposing said sorbent to regeneration conditions comprising a quantity of oxygen and a temperature effective to regenerate said sorbent.

80. The process of claim 74 wherein said regenerating comprises exposing said sorbent to regeneration conditions comprising a quantity of oxygen and a temperature effective to regenerate said sorbent.

81. The process of claim 75 wherein said regenerating comprises exposing said sorbent to regeneration conditions comprising a quantity of oxygen and a temperature effective to regenerate said sorbent.

82. The process of claim 76 wherein said regenerating comprises exposing said sorbent to regeneration conditions comprising a quantity of oxygen and a temperature effective to regenerate said sorbent.

83. The process of claim 77 wherein said regenerating comprises exposing said sorbent to regeneration conditions comprising a quantity of oxygen and a temperature effective to regenerate said sorbent.

84. The process of claim 78 wherein said regenerating comprises exposing said sorbent to regeneration conditions comprising a quantity of oxygen and a temperature effective to regenerate said sorbent.

85. The process of claim 45 wherein said converting comprises hydroformylating said skeletally isomerized olefin.

86. The process of claim 46 wherein said converting comprises hydroformylating said skeletally isomerized olefin.

87. The process of claim 47 wherein said converting comprises hydroformylating said skeletally isomerized olefin.

88. The process of claim 48 wherein said converting comprises hydroformylating said skeletally isomerized olefin.

89. The process of claim 49 wherein said converting comprises hydroformylating said skeletally isomerized olefin.

90. The process of claim 50 wherein said converting comprises hydroformylating said skeletally isomerized olefin.

91. The process of claim 45 wherein said purified olefin feed consists of about 1 ppm or less of said phosphorous-containing impurities.

92. The process of claim 46 wherein said purified olefin feed consists of about 1 ppm or less of said phosphorous-containing impurities.

93. The process of claim 47 wherein said purified olefin feed consists of about 1 ppm or less of said phosphorous-containing impurities.

94. The process of claim 48 wherein said purified olefin feed consists of about 1 ppm or less of said phosphorous-containing impurities.

95. The process of claim 49 wherein said purified olefin feed consists of about 1 ppm or less of said phosphorous-containing impurities.

96. The process of claim 50 wherein said purified olefin feed consists of about 1 ppm or less of said phosphorous-containing impurities.

97. The process of claim 45 wherein said purified olefin feed consists of about 0.5 ppm or less of said phosphorous-containing impurities.

98. The process of claim 46 wherein said purified olefin feed consists of about 0.5 ppm or less of said phosphorous-containing impurities.

99. The process of claim 47 wherein said purified olefin feed consists of about 0.5 ppm ores of said phosphorous-containing impurities.

100. The process of claim 48 wherein said purified olefin feed consists of about 0.5 ppm or less of said phosphorous-containing impurities.

101. The process of claim 49 wherein said purified olefin feed consists of about 0.5 ppm or less of said phosphorous-containing impurities.

102. The process of claim 50 where said purified olefin feed consists of about 0.5 ppm or less of said phosphorous-containing impurities.

103. A process of making a branched primary alcohol composition, comprising:
    providing an olefin feed comprising a content of dienes;
    providing one or more sorbents selected from the group consisting of an acidic zeolite, an acidic alumina, a neutral alumina, and an activated carbon, said one or more sorbents being adapted to sorb a sufficient amount of dienes to produce a purified olefin feed; and
    contacting said olefin feed with said one or more sorbents under conditions and for a time effective to produce said purified olefin feed;

contacting said purified olefin feed with a skeletal isomerization catalyst under conditions effective to yield skeletally isomerized olefins; and converting said skeletally isomerized olefins into said primary alcohol composition.

104. The process of claim 103 wherein said sorbent comprises particles having a diameter of from about 0.8 mm (1/32 inch) to about 1.6 mm (1/16 inch).

105. The process of claim 103 wherein said sorbent comprises particles having a diameter of about 0.8 mm.

106. The process of claim 103 wherein said sorbent comprises alumina.

107. The process of claim 104 wherein said sorbent comprises alumina.

108. The process of claim 105 wherein said sorbent comprises alumina.

109. The process of claim 103 wherein said sorbent has a surface area of from about 100 m$^2$/g to about 900 m$^2$/g.

110. The process of claim 104 wherein said sorbent has a surface area of from about 100 m$^2$/g to about 900 m$^2$/g.

111. The process of claim 105 wherein said sorbent has a surface area of from about 100 m$^2$/g to about 900 m$^2$/g.

112. The process of claim 106 wherein said sorbent has a surface area of from about 100 m$^2$/g to about 900 m$^2$/g.

113. The process of claim 107 wherein said sorbent has a surface area of from about 100 m$^2$/g to about 900 m$^2$/g.

114. The process of claim 108 wherein said sorbent has a surface area of from about 100 m$^2$/g to about 900 m$^2$/g.

115. The process of claim 103 wherein said LHSV is from about 0.01 hr$^{-1}$ to about 10 hr$^{-1}$.

116. The process of claim 103 wherein said LHSV is from about 0.1 hr$^{-1}$ to about 1 hr$^{-1}$.

117. The process of claim 104 wherein said LHSV is from about 0.01 hr$^{-1}$ to about 10 hr$^{-1}$.

118. The process of claim 104 wherein said LHSV is from about 0.01 hr$^{-1}$ to about 1 hr$^{-1}$.

119. The process of claim 105 wherein said LHSV is from about 0.1 hr$^{-1}$ to about 10 hr$^{-1}$.

120. The process of claim 105 wherein said LHSV is from about 0.01 hr$^{-1}$ to about 1 hr$^{-1}$.

121. The process of claim 106 wherein said LHSV is from about 0.01 hr$^{-1}$ to about 10 hr$^{-1}$.

122. The process of claim 106 wherein said LHSV is from about 0.01 hr$^{-1}$ to about 1 hr$^{-1}$.

123. The process of claim 107 wherein said LHSV is from about 0.1 hr$^{-1}$ to about 10 hr$^{-1}$.

124. The process of claim 107 wherein said LHSV is from about 0.1 hr$^{-1}$ to about 1 hr$^{-1}$.

125. The process of claim 108 wherein said LHSV is from about 0.01 hr$^{-1}$ to about 10 hr$^{-1}$.

126. The process of claim 109 wherein said LHSV is from about 0.1 hr$^{-1}$ to about 1 hr$^{-1}$.

127. The process of claim 110 wherein said LHSV is from about 0.01 hr$^{-1}$ to about 10 hr$^{-1}$.

128. The process of claim 110 wherein said LHSV is from about 0.1 hr$^{-1}$ to about 1 hr$^{-1}$.

129. The process of claim 111 wherein said LHSV is from about 0.01 hr$^{-1}$ to about 10 hr$^{-1}$.

130. The process of claim 112 wherein said LHSV is from about 0.1 hr$^{-1}$ to about 1 hr$^{-1}$.

131. The process of claim 103 further comprising regenerating said sorbent.

132. The process of claim 104 further comprising regenerating said sorbent.

133. The process of claim 105 further comprising regenerating said sorbent.

134. The process of claim 106 further comprising regenerating said sorbent.

135. The process of claim 107 further comprising regenerating said sorbent.

136. The process of claim 108 further comprising regenerating said sorbent.

137. The process of claim 131 wherein said regenerating comprises exposing said sorbent to regeneration conditions comprising a quantity of oxygen and a temperature effective to regenerate said sorbent.

138. The process of claim 132 wherein said regenerating comprises exposing said sorbent to regeneration conditions comprising a quantity of oxygen and a temperature effective to regenerate said sorbent.

139. The process of claim 133 wherein said regenerating comprises exposing said sorbent to regeneration conditions comprising a quantity of oxygen and a temperature effective to regenerate said sorbent.

140. The process of claim 134 wherein said regenerating comprises exposing said sorbent to regeneration conditions comprising a quantity of oxygen and a temperature effective to regenerate said sorbent.

141. The process of claim 135 wherein said regenerating comprises exposing said sorbent to regeneration conditions comprising a quantity of oxygen and a temperature effective to regenerate said sorbent.

142. The process of claim 136 wherein said regenerating comprises exposing said sorbent to regeneration conditions comprising a quantity of oxygen and a temperature effective to regenerate said sorbent.

143. The process of claim 103 wherein said converting comprises hydroformylating said skeletally isomerized olefin.

144. The process of claim 104 wherein said converting comprises hydroformylating said skeletally isomerized olefin.

145. The process of claim 105 wherein said converting comprises hydroformylating said skeletally isomerized olefin.

146. The process of claim 106 wherein said converting comprises hydroformylating said skeletally isomerized olefin.

147. The process of claim 107 wherein said converting comprises hydroformylating said skeletally isomerized olefin.

148. The process of claim 108 wherein said converting comprises hydroformylating said skeletally isomerized olefin.

149. The process of claim 103 wherein said purified olefin feed consists of about 1 ppm or less of said phosphorous-containing impurities.

150. The process of claim 104 wherein said purified olefin feed consists of about 1 ppm or less of said phosphorous-containing impurities.

151. The process of claim 105 wherein said purified olefin feed consists of about 1 ppm or less of said phosphorous-containing impurities.

152. The process of claim 106 wherein said purified olefin feed consists of about 1 ppm or less of said phosphorous-containing impurities.

153. The process of claim 107 wherein said purified olefin feed consists of about 1 ppm or less of said phosphorous-containing impurities.

154. The process of claim 108 wherein said purified olefin feed consists of about 1 ppm or less of said phosphorous-containing impurities.

155. The process of claim 103 wherein said purified olefin feed consists of about 0.5 ppm or less of said phosphorous-containing impurities.

156. The process of claim 104 wherein said purified olefin feed consists of about 0.5 ppm or less of said phosphorous-containing impurities.

157. The process of claim 105 wherein said purified olefin feed consists of about 0.5 ppm or less of said phosphorous-containing impurities.

158. The process of claim 106 wherein said purified olefin feed consists of about 0.5 ppm or less of said phosphorous-containing impurities.

159. The process of claim 107 wherein said purified olefin feed consists of about 0.5 ppm or less of said phosphorous-containing impurities.

160. The process of claim 108 wherein said purified olefin feed consists of about 0.5 ppm or less of said phosphorous-containing impurities.

\* \* \* \* \*